United States Patent [19]

Darms et al.

[11] 4,140,703
[45] Feb. 20, 1979

[54] PHTHALIC ACID DERIVATIVES SUBSTITUTED BY ALKENYLAMINO GROUPS

[75] Inventors: Roland Darms, Therwil; Hubert Meindl, Riehen, both of Switzerland

[73] Assignee: Ciba-Geigy Corporation, Ardsley, N.Y.

[21] Appl. No.: 857,163

[22] Filed: Dec. 5, 1977

[30] Foreign Application Priority Data

Dec. 14, 1976 [CH] Switzerland ............... 15702/76

[51] Int. Cl.² ........................................... C07D 307/89
[52] U.S. Cl. ............................. 260/346.3; 260/501.11; 260/501.13; 562/458; 528/114; 528/365; 528/322
[58] Field of Search ............ 260/346.3, 501.11, 501.13, 260/518 R

[56] References Cited

U.S. PATENT DOCUMENTS

| | | | |
|---|---|---|---|
| Re. 29,316 | 7/1977 | Bargain et al. | 260/30.2 |
| 2,597,965 | 5/1952 | Adams | 560/19 X |
| 3,562,223 | 2/1971 | Bargain et al. | 260/78 |
| 3,658,764 | 4/1972 | Bargain et al. | 260/78 UA |
| 3,836,571 | 9/1974 | Skoultchi et al. | 560/19 |
| 4,035,345 | 7/1977 | Ducloux et al. | 260/78 UA |
| 4,078,142 | 3/1978 | Keske | 260/346.3 X |

FOREIGN PATENT DOCUMENTS 699122 10/1973 United Kingdom ............... 260/346.3

*Primary Examiner*—Richard Raymond
*Attorney, Agent, or Firm*—Luther A. R. Hall

[57] ABSTRACT

Novel phthalic acid derivatives, especially phthalic anhydrides, which are substituted by alkenylamino groups, and a process for their preparation are described. The novel phthalic acid derivatives are valuable intermediates for the preparation of corresponding esters, ester-amides or imides, which, in turn, are used in hot-curable mixtures which are stable on storage and have improved processing characteristics, in particular a prolonged pot life, for the production of mouldings of various types. Phthalic anhydrides substituted by alkenylamino groups, according to the invention, are also suitable as curing agents for epoxide resins. Products or materials cured therewith are distinguished by good mechanical and/or electrical properties.

5 Claims, No Drawings

PHTHALIC ACID DERIVATIVES SUBSTITUTED BY ALKENYLAMINO GROUPS

The present invention relates to novel phthalic acid derivatives, especially phthalic anhydrides, which are substituted by alkenylamino groups, a process for their preparation and the use of the phthalic acid anhydrides substituted by alkenylamino groups for curing epoxide resins.

The novel phthalic acid derivatives are of the formula I

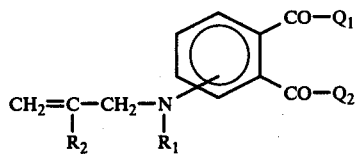

in which $Q_1$ and $Q_2$ independently of one another are —OH or $O^-M^+$, or $Q_1$ and $Q_2$ together form the grouping —O— or $[-O^-]_2M_1^{++}$, $R_1$ is hydrogen or

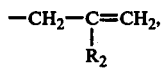

$R_2$ is hydrogen or methyl, $M^+$ is an alkali metal cation, a trialkylammonium cation having 3–24 and especially 3–12 carbon atoms or a quaternary ammonium cation and $M_1^{++}$ is an alkaline earth metal cation.

The phthalic acid derivatives of the formula I can also be in the form of mixtures of the 3- and 4-isomers.

The phthalic acid derivatives of the formula I can be obtained by reacting a compound of the formula II

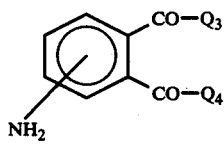

with a compound of the formula III

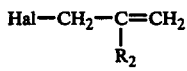

to give a phthalic acid derivative of the formula I'

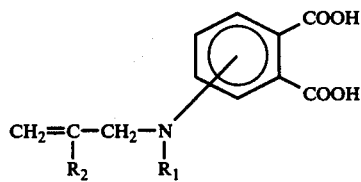

in which formulae $Q_3$ and $Q_4$ independently of one another are —OH or a group $-O^-M^+$, or $Q_3$ and $Q_4$ together are $[-O^-]_2M_1^{++}$, and Hal is a halogen atom, such as chlorine, bromine or iodine, and $R_1$, $R_2$, $M^+$ and $M_1^{++}$ are as defined under formula I, and, if desired, subsequently converting the resulting phthalic acid of the formula I' into another derivative of the formula I.

If $Q_1$, $Q_2$, $Q_3$ or $Q_4$ denotes a group $-O^-M^+$, $M^+$ is, for example, the lithium, sodium, potassium, trimethylammonium, triethylammonium, methyl-diethylammonium or tri-n-octylammonium cation. Examples of quaternary ammonium cations $M^+$ are the benzyltrimethylammonium cation and the tetramethylammonium cation. $M^+$ is preferably the sodium cation.

Possible alkaline earth metal cations $M_1^{++}$ are, for example, the calcium cation or magnesium cation.

The grouping

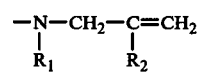

(formula I or I') and the amino group in formula II are preferably in the ortho-position relative to the —$COQ_1$ or —$COQ_2$ group or to a —COOH group and, respectively, in the ortho-position relative to the —$COQ_3$ or —$COQ_4$ group. $Q_1$ and $Q_2$, or $Q_3$ and $Q_4$, preferably have the same meaning.

Compounds of the formula I in which $Q_1$ and $Q_2$ together form the grouping —O—, $R_2$ is hydrogen and $R_1$ is —$CH_2$—CH=$CH_2$ are particularly preferred.

The starting material of the formula II which are used are preferably those in which $Q_3$ and $Q_4$ are each a group —$O^-M^+$, or $Q_3$ and $Q_4$ together are the grouping $[-O^-]_2M_1^{++}$, $M^+$ being an alkali metal cation, especially the sodium cation, and $M_1^{++}$ being the calcium or magnesium cation. Hal in formula III is preferably chlorine or bromine.

The starting materials of the formulae II and III are known per se or can be prepared in a manner which is known per se. They are appropriately reacted with one another in a polar medium, especially in an aqueous medium, at temperatures between about 0° and 100° C. and especially between about 25° and 80° C., and preferably in the presence of a base, such as alkali metal carbonates or alkali metal hydroxides, for example potassium carbonate, potassium hydroxide or sodium hydroxide.

After the reaction has ended, the phthalic acid of the formula I' which has formed can be precipitated by adding an aqueous mineral acid, such as aqueous hydrochloric acid, aqueous sulphuric acid or aqueous phosphoric acid, and subsequently converted, if desired, into another derivative of the formula I.

The cyclisation to anhydrides of the formula I ($Q_1$ and $Q_2$ together = —O—) can be effected in a manner which is known per se, chemically or by the action of heat. The chemical cyclisation is appropriately carried out at temperatures of about 25° to 130° C. in the presence of conventional dehydrating agents. Dehydrating agents which can be used are, in particular, anhydrides of aliphatic monocarboxylic acids having 2–5 carbon atoms, which are unsubstituted or substituted by halogen atoms or alkyl groups, such as acetic anhydride and propionic anhydride, trifluoroacetic anhydride, trimethylacetic anhydride or triethylacetic anhydride. However, cyclisation by the action of heat is preferred. For this purpose, the phthalic acids of the formula I' are advantageously heated to temperatures between about 120° and 180° C.

Compounds of the formula I in which $Q_1$ and/or $Q_2$ is a group —$O^-M^+$, or $Q_1$ and $Q_2$ together are $(-O^-)_2M_1^{++}$, can be obtained by reacting the phthalic acids of the formula I' with suitable bases, such as NaOH or Ca(OH)$_2$.

The componds, according to the invention, of the formula I can be isolated and purified in a conventional manner, for example by precipitation with acids as indicated above, by extraction with suitable solvents, such as benzene or toluene, by distillation or by recrystallisation from organic solvents, for example mixtures of toluene and n-hexane.

The phthalic acid derivatives, according to the invention, of the formula I are valuable intermediates for the preparation of corresponding esters, ester-amides or imides, which, in turn, are used in hot-curable mixtures which are stable on storage and have improved processing characteristics, especially a prolonged pot life, for the production of mouldings of various types, in particular castings.

Phthalic anhydrides according to the invention ($Q_1$ and $Q_2$ together = —O—) are also suitable as curing agents for epoxide resins. Products or materials cured with these anhydrides are distinguished by good mechanical and/or electrical properties, in particular by a high heat distortion resistance associated, at the same time, with good flexural strength and also by low dielectric loss factors at elevated temperatures.

The present application thus also relates to curable mixtures which are suitable for the production of mouldings, impregnations, coatings, glue bonds and the like. These curable mixtures are mixtures which contain (a) a polyepoxide compound, (b) as the curing agent at least one compound of the formula I in which $Q_1$ and $Q_2$ together form the grouping —O— and (c) if desired further additives.

Appropriately, 0.5 to 1.5 mols, preferably about 0.9 to 1.0 mol, of a phthalic anhydride of the formula I are used per 1 equivalent of epoxide group in the polyepoxide compound (a).

Compounds which can be used as polyepoxide compounds (a) are all those which can be cured with anhydride curing agents. Particularly preferred compounds are: alicyclic polyepoxides, such as epoxyethyl-3,4-epoxycyclohexane (vinyl cyclohexene diepoxide), limonene diepoxide, dicyclopentadiene diepoxide, bis-(3,4-epoxycyclohexylmethyl) adipate, 3',4'-epoxycyclohexylmethyl 3,4-epoxycyclohexane carboxylate, 3',4'-epoxy-6'-methylcyclohexylmethyl 3,4-epoxy-6-methylcyclohexane carboxylate, 3-(3',4'-epoxycyclohexyl)-2,4-dioxaspiro-(5,5)-8,9-epoxyundecane and 3-(glycidyloxyethoxyethyl)-2,4-dioxaspiro(5,5)-8,9-epoxyundecane; di- or poly-glycidyl ethers of polyhydric alcohols, such as 1,4-butanediol or polyalkylene glycols, such as polypropylene glycols; di- or poly-glycidyl ethers of cycloaliphatic polyols, such as 2,2-bis-(4-hydroxycyclohexyl)-propane; di- or poly-glycidyl ethers of polyhydric phenols, such as resorcinol, bis-(p-hydroxyphenyl)methane, 2,2-bis-(p-hydroxyphenyl)-propane (diomethane), 2,2-bis-(4'-hydroxy- 3',5'-dibromophenyl)-propane and 1,1,2,2-tetrakis-(p-hydroxyphenyl)-ethane, or condensation products of phenols and formaldehyde which are obtained under acid conditions, such as phenol novolacs and cresol novolacs; and also di- or poly-($\beta$-methylglycidyl) ethers of the above-mentioned polyalcohols and polyphenols; polyglycidyl esters and poly-($\beta$-methylglycidyl) esters of polybasic carboxylic acids, such as phthalic acid, terephthalic acid, tetrahydrophthalic acid and hexahydrophthalic acid; and N-glycidyl derivatives of amines, amides and heterocyclic nitrogen bases, such as N,N-diglycidylaniline, N,N-diglycidyltoluidine, N,N,N',N'-tetraglycidyl-bis-(p-aminophenyl)-methane; triglycidyl isocyanurate; N,N'-diglycidylethyleneurea; N,N'-diglycidyl-5,5-dimethylhydantoin and N,N'-diglycidyl-5-isopropyl-hydantoin; and N,N'-diglycidyl-5,5-dimethyl-6-iso-propyl-5,6-dihydrouracil.

If desired, active diluents, for example styrene oxide, butyl glycidyl ether, isooctyl glycidyl ether, phenyl glycidyl ether, cresyl glycidyl ether or glycidyl esters of synthetic, highly branched and, in the main, tertiary, aliphatic monocarboxylic acids, can be added to the curable mixtures in order to lower the viscosity.

Curing accelerators can also be employed during curing; such accelerators are, for example, tertiary amines, their salts or quaternary ammonium compounds, for example 2,4,6-tris-(dimethylaminomethyl)-phenol, benzyldimethylamine, 1-methylimidazole, 2-ethyl-4-methyl-imidazole, 4-aminopyridine and triamylammonium phenolate; or alkali metal alcholates, for example sodium hexanetriolate. Curing of the mixtures according to the invention is appropriately carried out in the temperature range of 50° C. to 250° C. and preferably of 130°–220° C.

Curing can also be carried out in a known manner as a two-stage or multi-stage process, the first curing stage being carried out at low temperature and post-curing being carried out at a higher temperature.

If desired, curing can also be carried out in two stages in a manner such that the curing reaction is first prematurely discontinued or the first stage is carried out at a slightly elevated temperature, in which case a curable precondensate which is still fusible and/or soluble (so-called "B-stage") of the epoxide component (a) and the curing agent (b) is obtained. A precondensate of this type can be used, for example, to produce "prepregs", moulding compositions or, especially, sintering powders.

As it is used here, the term "curing" means the conversion of the soluble polyepoxides which are either liquid or fusible into solid, insoluble and non-fusible, three-dimensionally crosslinked products or materials, this conversion being effected in particular, as a rule, with simultaneous shaping to give mouldings, such as castings, compression mouldings and laminates or to give impregnations, coatings, lacquer films or glue bonds.

The mixtures according to the invention can contain, as further additives (c), in particular vinyl compounds, unsaturated bis-imidyl derivatives or also phthalimides, phthalic acid diesters or phthalic acid ester-amides prepared from phthalic acid derivatives according to the invention.

Vinyl compounds which can be used are, for example, those of the formula IV

in which $Z_1$ and $Z_3$ are each hydrogen, $Z_2$ is hydrogen, chlorine or methyl and $Z_4$ is —CN, —COOH, —CONH$_2$, phenyl, methylphenyl, methoxyphenyl, cyclohexyl, pyridyl, imidazolyl, pyrrolidonyl, —COO-alkyl having 1–12 carbon atoms in the alkyl part, —COO—phenyl,

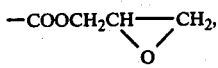

—COO-alkyl-OH having 1-3 carbon atoms in the alkyl part, —OCO-alkyl having 1-4 carbon atoms in the alkyl part, —OCO-phenyl, —CO-alkyl having 1-3 carbon atoms in the alkyl part, alkoxy having 1-6 carbon atoms, phenoxy or

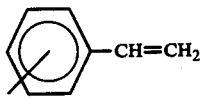

or $Z_1$ and $Z_2$ are each hydrogen and $Z_3$ and $Z_4$ together form the grouping

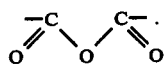

Examples of such vinyl compounds which may be mentioned are: acrylic acid, methacrylic acid, acrylonitrile, methacrylonitrile, chloracrylonitrile, styrene, methylstyrenes substituted in the nucleus, 4-methoxystyrene, vinylcyclohexane, methyl acrylate and methacrylate, ethyl acrylate and methacrylate, isopropyl acrylate and methacrylate, 2-ethylhexyl acrylate and methacrylate and phenyl acrylate and methacrylate, vinyl acetate and vinyl propionate, 2,3-epoxypropyl acrylate and 2,3-epoxypropyl methacrylate, vinyl benzoate, 2-vinylpyridine, 4-vinylpyridine, vinylimidazole, vinylpyrrolidone, methyl vinyl ketone, ethyl vinyl ketone, ethyl vinyl ether, n-butyl vinyl ether and divinylbenzene.

Mixtures of several vinyl compounds of the formula IV can also be used.

Vinyl cpompounds of the formula IV which are preferably used are those in which $Z_1$ and $Z_3$ are each hydrogen, $Z_2$ is hydrogen or methyl and $Z_4$ is —COO-alkyl having 1-10 carbon atoms in the alkyl part, or $Z_1$, $Z_2$ and $Z_3$ are each hydrogen and $Z_4$ is —CN, phenyl or —OCOCH$_3$.

Unsaturated bis-imidyl derivatives which can be used are, for example, those of the formula V

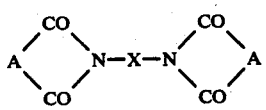

in which X is a divalent bridge member having 2-30 carbon atoms and A is —CH═CH,

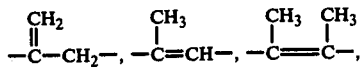

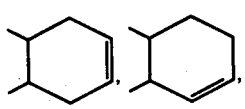

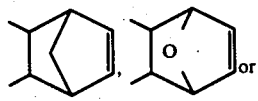

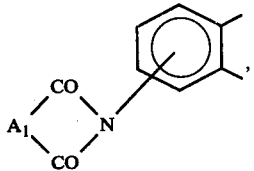

in which $A_1$ can have the same meanings as A except for the last-mentioned meaning.

Possible bridge members X are, especially, alkylene groups having 1-12, and especially 2-6, carbon atoms, phenylene or naphthylene groups which are unsubstituted or substituted by halogen atoms, such as chlorine, fluorine or bromine, or alkyl or alkoxy groups having 1-4, and especially 1 or 2, carbon atoms, cyclohexylene groups and also groups of the formulae

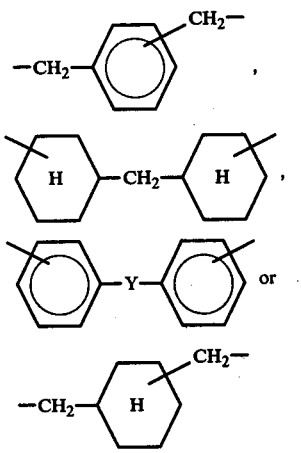

in which Y is —CH$_2$—, —O—, —S—, —SO—, —SO$_2$— or

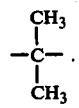

Compounds of the formula V in which A is a group of the formulae —CH═CH—,

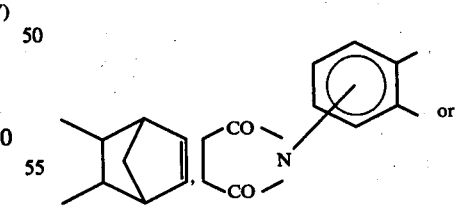

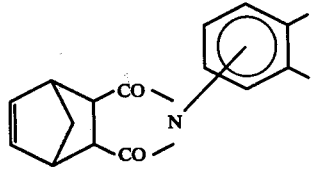

and X is a 4,4'-diphenylmethane or 4,4'-diphenyl ether radical are particularly preferred.

Phthalimides, phthalic acid diesters or phthalic acid ester-amides, prepared from phthalic acid derivatives according to the invention, which can be employed are, for example, compounds of the formula VI or VII.

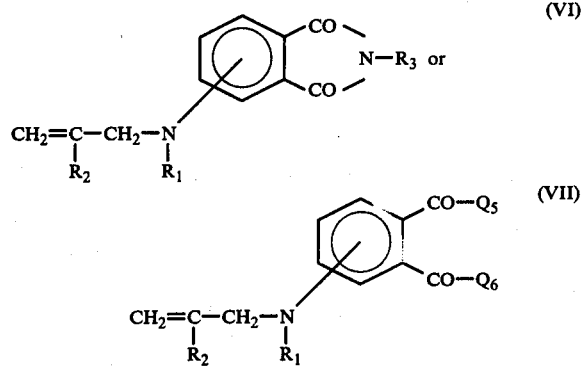

in which $R_3$ is alkyl having 1-4 C atoms, allyl, phenyl or a grouping

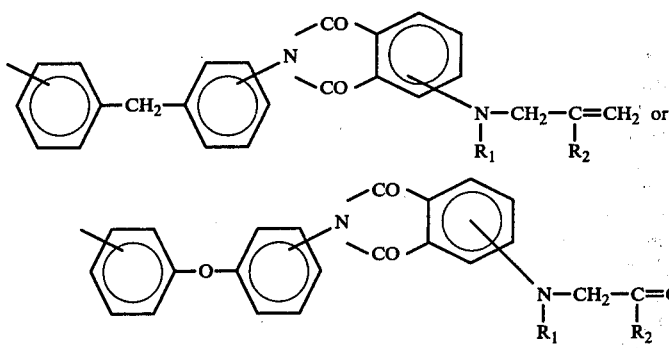

one of $Q_5$ and $Q_6$ is $-OR_4$ and the other is $-OR_5$ or

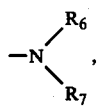

$R_4$, $R_5$, $R_6$ and $R_7$ independently of one another are alkyl having 1-8 C atoms or allyl and $R_1$ and $R_2$ are as defined under formula I.

The compounds of the formula VI can be prepared in a manner which is known per se, for example by reacting compounds of the formula I in which $Q_1$ and $Q_2$ together are the grouping —O— with the corresponding amines. Phthalic acid diesters or phthalic acid esteramides of the formula VII can be obtained, for example, by reacting compounds of the formula I in which $Q_1$ and $Q_2$ together form the grouping —O—, in the presence of an inorganic or organic base, first with an alcohol HO-$R_5$ and then with an amine

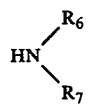

and/or with a halide which introduces the radical $R_4$.

By the addition of compounds of the formulae IV to VII to the curable mixtures according to the invention it is possible to change the processing characteristics of these mixtures and to obtain novel interesting modifications in the physical properties of the cured mouldings thus obtainable. The said compounds of the formulae IV to VII are appropriately employed in amounts of about 5-50 mol %, and especially of about 10-35 mol %, relative to the phthalic anhydride of the formula I.

Depending on the intended use, cationic, anionic or free radical polymerisation initiators which are known per se can also be added to the mixtures according to the invention. In general, these polymerisation initiators are used in an amount of about 0.01 to 5 percent by weight and preferably of 0.01 to 1.5 percent by weight, relative to the total weight of the reactants. Free radical initiators, such as inorganic or organic peroxides or azo compounds, for example hydrogen peroxide, potassium peroxydisulphate, tert.-butyl hydroperoxide, di-tert.-butyl peroxide, peracetic acid, benzoyl peroxide, diacyl peroxides, cumene hydroperoxide, tert.-butyl perbenzoate, tert.-alkyl peroxycarbonates and α,α'-azoisobutyronitrile, are preferred. In general, however, the addition of polymerisation initiators can be omitted.

The curable mixtures according to the invention can also contain suitable plasticisers, such as dibutyl phthalate, dioctyl phthalate or tricresyl phthalate.

Finally, extenders, fillers and reinforcing agents, for example coal tar, bitumen, textile fibres, glass fibres, asbestos fibres, boron fibres, carbon fibres, mineral silicates, mica, quartz powder, titanium dioxide, aluminium oxide hydrate, bentonites, kaolin, silica aerogel or metal powders, such as aluminium powder or iron powder, and also pigments and dyes, such as carbon black, oxide pigments, titanium oxide and others, can be added to the curable mixtures according to the invention in any stage before curing. Furthermore, other customary additives, for example flameproofing agents, such as antimony trioxide, agents for conferring thixotropy, flow control agents, such as silicones, waxes or stearates (some of which are also used as mould release agents) can also be added to the curable mixtures.

The curable mixtures according to the invention can be produced in a conventional manner with the aid of known mixing equipment (stirrers, kneaders, mills and the like).

The curable epoxide resin mixtures according to the invention are employed, in particular, in the fields of surface protection, and the electrical industry, laminating processes and the building trade. They can be used in a formulation suited in each case to the special end use, in the unfilled or filled state, as paints, lacquers, compression moulding compositions, dipping resins, casting resins, injection moulding formulations, impregnating resins and adhesives and as tool resins, laminating resins, sealing and filling compositions, floor covering compositions and binders for mineral aggregates.

The following epoxide resin was used for the preparation, described in the use examples, of curable mixtures:

EPOXIDE RESIN A

An epoxide resin (technical product) prepared by a condensation reaction of 2,2-bis-(p-hydroxyphenyl)-propane with a stoichiometric excess of epichlorohydrin in the presence of alkali, which consists in the main of the monomeric diglycidyl ether of the formula

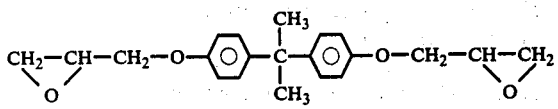

and is liquid at room temperature and has an epoxide content of 5.12–5.54 epoxide equivalent/kg. Viscosity (Hoeppler) at 25° C.: 9,000–13,000 cP.

For determination of the mechanical properties of the curable mixtures described in the examples which follow, 4 mm thick sheets were produced. The test specimens for the determination of the heat distortion according to ISO/R 75 (DIN 53,461), and the flexural strength and deflection according to VSM 77,103 were machined from the sheets.

2 mm thick sheets were produced for determination of the electrical properties (dielectric loss factor according to DIN 53,483, dielectric constant according to DIN 53,483 and specific volume resistivity according to DIN 53,482).

PREPARATION EXAMPLES

EXAMPLE 1

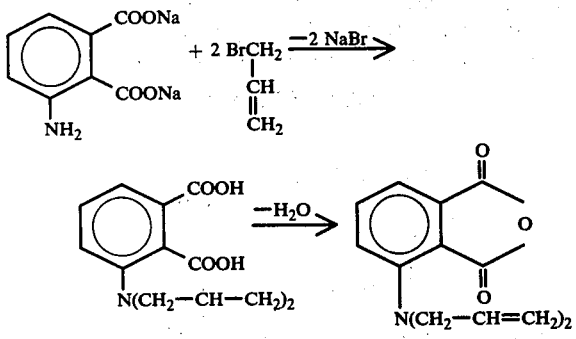

225 g (1.0 mol) of disodium 3-aminophthalate and 138 g (1.0 mol) of potassium carbonate are dissolved in 400 ml of water. 317.2 g (2.6 mols) of allyl bromide are added to the solution at about 25° C. and the reaction mixture is stirred for 4 hours at 30°–35° C. After adding 200 ml of 35% strength aqueous hydrochloric acid, the diallylaminophthalic acid is precipitated. The product is filtered off at 10° C., washed with 100 ml of water and dried. Yield: 222 g = 85% of theory. 261 g (1 mol) of the resulting 3-N,N-diallylaminophthalic acid are heated to 150°–155° C. A melt forms and this is stirred for 2 hours at about 150° C. while a stream of nitrogen is passed over and is then allowed to cool to 50° C. 750 ml of toluene and 750 ml of n-hexane are then added and the crude product is recrystallised from this mixture. This gives 237 g of 3-N,N-diallylaminophthalic anhydride; melting point 94°–95° C.

Analysis for $C_{14}H_{13}NO_3$: calculated C 69.13%: H 5.39%: N 5.76%. found C 68.90%: H 5.40%: N 5.72%.

If, in the above example, the allyl bromide is replaced by an equimolecular amount of allyl chloride, 3-diallylaminophthalic acid is again obtained and this is converted into the anhydride in the same way.

If, in the above example, 1.0 mol of allyl bromide or allyl chloride is used in place of an excess of allyl bromide or allyl chloride and in other respects the procedure is identical, this gives 3-N-allylaminophthalic anhydride; melting point 116°–117° C.

Analysis for $C_{11}H_9NO_3$: calculated C 65.0%: H 4.4%: N 6.9%. found C 64.8%: H 4.6%: N 6.9%.

EXAMPLE 2

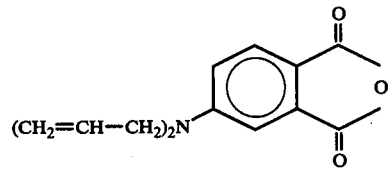

225 g (1.0 mol) of disodium 4-aminophthalate are reacted with 317.2 g (2.6 mols) of allyl bromide in the manner indicated in Example 1. This gives 196 g = 75% of theory of 4-N,N-diallylaminophthalic acid. 261 g (1.0 mol) of 4-N,N-diallylaminophthalic acid are converted into 4-N,N-diallylaminophthalic anhydride under the conditions described in Example 1.

Yield: 214 g = 88% of theory, melting point 63–64° C.

Analysis for $C_{14}H_{13}NO_3$: calculated C 69.13%: H 5.39%: N 5.76%. found C 69.00%: H 5.50%: N 5.66%.

If, in place of disodium 3-aminophthalate or disodium 4-aminophthalate, a 1:1 isomer mixture of the two compounds is employed and in other respects the procedure is as indicated in Example 1, this gives a 1:1 mixture of 3- and 4-N,N-diallylaminophthalic anhydride.

EXAMPLE 3

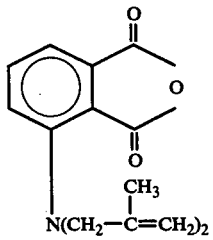

22.5 g (0.1 mol) of disodium 3-aminophthalate are dissolved in 150 ml of water. 18.1 g (0.2 mol) of methallyl chloride are added to the solution and the mixture is allowed to react for 3 hours at 70°–75° C., with stirring. The pH value of the reaction solution is kept above 4 by adding aqueous sodium hydroxide solution (consumption: 10 ml of a solution of 40 g of sodium hydroxide in 100 ml of water). After the reaction has ended, the pH is adjusted to 0.5–1.0 by adding 20 ml of hydrochloric acid (35% strength aqueous solution). The reaction mixture is evaporated to dryness and the residue is then heated at 150°–160° C. for 2 hours. The resulting 3-N,N-di-(methylallyl)-amino-phthalic anhydride is separated from the sodium chloride by extraction with 200 ml of toluene. The toluene is then distilled off and the oily crude product is subjected to vacuum distillation. This gives 12.4 g (45% of theory) of 3-N,N-di-(methylallylamino)-phthalic anhydride; boiling point under 0.01 mm, 123-127° C.

Analysis for $C_{16}H_{17}NO_3$: calculated C 70.8%: H 6.3%: N 5.2%. found C 70.8%: H 6.2%: N 5.3%.

Use Examples

EXAMPLE I 14.55 g of epoxide resin A (epoxide content 5.12 epoxide equivalents per kg) and 16.42 g of the 3-N,N-diallylaminophthalic anhydride prepared according to Example 1 (corresponding to 0.9 mol of the anhydride per 1 equivalent of epoxide groups) are mixed and the mixture is warmed to 100° C. in the course of 5 minutes, with stirring. A clear solution forms and this is cast into an aluminium mould preheated to 150° C. in order to produce sheets 4 mm and 2 mm thick. Curing is effected in a circulating air oven, first for 3 hours at 150° C. and then for 5 hours at 220° C. This gives bubble-free castings having good mechanical and electrical properties.

EXAMPLE II

In a manner analogous to that described in Example I, 9.70 g of epoxide resin A (epoxide content 5.12 epoxide equivalents per kg) and 10.95 g of the 4-N,N-diallylaminophthalic anhydride prepared according to Example 2 (corresponding to 0.9 mol of the anhydride per 1 equivalent of epoxide groups) are mixed and the mixture is processed to bubble-free, transparent castings.

EXAMPLE III 28.83 g of epoxide resin A (epoxide content 5.12 epoxide equivalents per kg) and 32.80 g of a 1:1 mixture of 3-N,N-diallylaminophthalic anhydride and 4-N,N-diallylaminophthalic anhydride (prepared according to Example 2, final paragraph), (corresponding to 0.9 mol of anhydride per 1 equivalent of epoxide groups) are mixed and the mixture is warmed to 80° C. in the course of 10 minutes, with stirring. A clear solution forms and this is processed to bubble-free castings analogously to Example I.

Some mechanical and electrical properties of the castings according to Examples I–III are summarised in the table which follows.

Table

| Mechanical/electrical properties | Casting according to | | |
|---|---|---|---|
| | Example I | Example II | Example III |
| Heat distortion resistance according to ISO/R 75 (= DIN 53,461) ° C | 186 | — | 175 |
| Flexural strength according to VSM 77,103 N/mm² | 110 | — | 92 |
| Deflection according to VSM 77,103, mm | 5 | — | 4 |
| Dielectric loss factor according to DIN 53,483 (tg δ at 180° C, 50 Hz) | 0.013 | 0.022 | 0.019 |
| Dielectric constant according to DIN 53,483 (ε) at 180° C | 3.7 | 4.0 | 3.9 |

VSM = Verein Schweizerischer Maschinenindustrieller
DIN = Deutsche Industrie-Norm
ISO/R = International Standards Organisation/Recommendations

EXAMPLE IV 14.42 g of epoxide resin A (epoxide content 5.20 epoxide equivalents per kg) and 16.40 g (0.0675 mol) of 4-N,N-diallylaminophthalic anhydride (corresponding to 0.9 mol of the anhydride per 1 equivalent of epoxide groups) are mixed and the mixture is warmed to 150° C. in the course of 10 minutes, with stirring. A clear solution forms and 5.37 g (0.015 mol) of 4,4'-bis-maleimidodiphenylmethane are then added and this dissolves after a few minutes. In order to produce sheets, the resulting solution is cast into an aluminium mould, and cured, in accordance with the procedure described in Example I. Transparent, firm castings are obtained.

EXAMPLE V 14.42 g of epoxide resin A (epoxide content 5.20 epoxide equivalents per kg), 16.40 g (0.0675 mol) of 4-N,N-diallylaminophthalic anhydride (corresponding to 0.9 mol of the anhydride per 1 equivalent of epoxide groups) and 2.11 g (0.0075 mol) of 3-N,N-diallylaminophthalic acid allylimide are mixed and the mixture is warmed to 150° C. in the course of 10 minutes, with stirring. A clear solution forms and this is processed to bubble-free, transparent and firm castings as described in Example I. The preparation of the above 3-N,N-diallylaminophthalic acid allylimide is described in Example VII.

EXAMPLE VI 14.42 g of epoxide resin A (epoxide content 5.20 epoxide equivalents per kg) and 16.40 g (0.0675 mol) of 3-N,N-diallylaminophthalic anhydride (corresponding to 0.9 mol of the anhydride per 1 equivalent of epoxide groups) are dissolved at 150° C. 2.34 g (0.0225 mol) of freshly distilled styrene are added to the resulting solution. The solution is then processed as described in Example I to give bubble-free, transparent castings.

As already mentioned, the phthalic acid derivatives according to the invention are also suitable for the preparation of corresponding esters, ester-amides and imides, which are used in mixtures according to the invention (c.f. Example V) or in hot-curable mixtures which are stable on storage and have a prolonged pot life. This latter use is illustrated by the examples which follow:

EXAMPLE VII

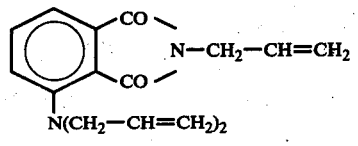

8.6 g (0.15 mol) of allylamine are added to a solution of 24.3 g (0.1 mol) of the 3-N,N-diallylaminophthalic anhydride prepared according to Example 1 in 200 ml of toluene, and the resulting mixture is stirred at 75°–80° C. for 2 hours. The toluene is then distilled off and the residue is stirred for 1 hour at 150°–160° C. The melt, which solidified on cooling, is recrystallised from 120 ml of special boiling point gasoline (mixture of hydrocarbons; boiling point 110°–130° C.).

This gives 17.6 g (81.5% of theory) of 3-N,N-diallylaminophthalic acid allylimide; melting point 74° C.

19.33 g (0.054 mol) of 4,4'-bis-maleimidyldiphenylmethane and 1.69 g (0.006 mol) of the above 3-N,N-diallylaminophthalic acid allylimide are mixed together well and the mixture is heated to 165° C., with occasional stirring. A melt forms and this is cast into an aluminium foil preheated to 180° C. in order to produce 4 mm thick sheets.

Curing is effected in a circulating air oven for 16 hours at 180° C. Transparent, bubble-free castings having good physical, mechanical and electrical properties are obtained. A lengthening of the pot life by about 60% is achieved by the addition of the above allyl derivative to the bis-imide.

EXAMPLE VIII

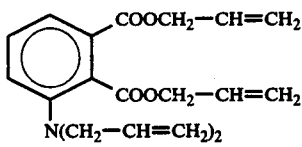

11.6 g (0.2 mol) of allyl alcohol and 20.3 g (0.2 mol) of triethylamine are added successively to a solution of 24.3 g (0.1 mol) of the 3-N,N-diallylaminophthalic anhydride prepared according to Example 1 in 50 ml of toluene. The resulting mixture is stirred at about 60° C. for 30 minutes and 24.4 g (0.2 mol) of allyl bromide are then added dropwise. After the exothermic reaction has subsided, the mixture is stirred for a further 1 hour at 50°-60° C. and is then cooled to 20° C. and the dissolved product is separated from the triethylammonium bromide, which has precipitated, by filtration. Subsequently, the toluene is first distilled off and the oily residue is then purified by vacuum distillation. This gives 27.6 g (81% of theory) of 1,2-diallyl 3-N,N-diallylaminophthalate; boiling point under 0.01 mm: 143°-145° C.

12.89 g (0.036 mol) of 4,4'-bis-maleimidyl-diphenylmethane and 1.36 g (0.004 mol) of the above 1,2-diallyl 3-N,N-diallylaminophthalate are mixed together well and the mixture is heated to 155° C., with occasional stirring. A melt of low viscosity forms after a few minutes and this is kept at 155° C. for 12 minutes. The gelled mixture resulting at the end of this time is allowed to cool and ground to a fine powder. This is introduced into a compression mould for circular sheets which has been preheated to 250° C. for processing by compression process and is pressed at this temperature for 20 minutes under a pressure of 350 kp/cm². A transparent, firm sheet having good electrical properties is obtained.

What is claimed is:

1. A phthalic acid derivative of the formula I

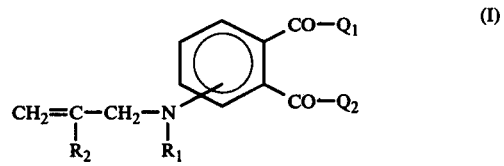

in which $Q_1$ and $Q_2$ independently of one another are —OH or —O$^-$M$^+$, or $Q_1$ and $Q_2$ together form the grouping —O— or [—O$^-$]$_2$M$_1^{++}$, $R_1$ is hydrogen or

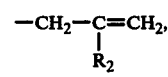

$R_2$ is hydrogen or methyl, M$^+$ is an alkali metal cation, a trialkylammonium cation having 3–24 carbon atoms or a quaternary ammonium cation and $M_1^{++}$ is an alkaline earth metal cation.

2. A phthalic acid derivative of the formula I according to claim 1, in which the grouping

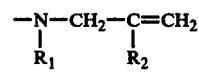

is in the orthoposition relative to the —COQ$_1$ or —COQ$_2$ group.

3. A phthalic acid derivative of the formula I according to claim 1, in which $Q_1$ and $Q_2$ together form the grouping —O—, $R_2$ is hydrogen and $R_1$ is —CH$_2$—CH=CH$_2$.

4. A phthalic acid derivative according to claim 1 of the formula

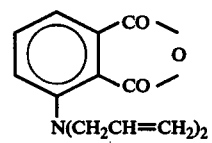

5. A phthalic acid derivative according to claim 1 of the formula

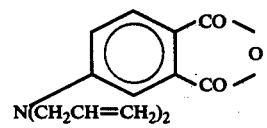

* * * * *